United States Patent
Liphardt et al.

(10) Patent No.: US 8,159,672 B1
(45) Date of Patent: *Apr. 17, 2012

(54) SAMPLE INVESTIGATING SYSTEM AND METHOD OF USE

(75) Inventors: Martin M. Liphardt, Lincoln, NE (US); Thomas E. Tiwald, Lincoln, NE (US); Blaine D. Johs, Lincoln, NE (US); Jeffrey S. Hale, Lincoln, NE (US); Craig M. Herzinger, Lincoln, NE (US); Steven E. Green, Lincoln, NE (US); Ping He, Lincoln, NE (US); Ronald A. Synowicki, Lincoln, NE (US); John A. Woollam, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 276 days.

This patent is subject to a terminal disclaimer.

(21) Appl. No.: 12/592,015

(22) Filed: Nov. 19, 2009

Related U.S. Application Data

(63) Continuation-in-part of application No. 11/452,483, filed on Jun. 14, 2006, now Pat. No. 7,623,237.

(60) Provisional application No. 60/691,297, filed on Jun. 17, 2005, provisional application No. 60/790,588, filed on Apr. 10, 2006.

(51) Int. Cl. *G01J 4/00* (2006.01)

(52) U.S. Cl. ..................... 356/369; 356/364

(58) Field of Classification Search ............. 356/364, 356/369

See application file for complete search history.

(56) References Cited

U.S. PATENT DOCUMENTS

| | | | | |
|---|---|---|---|---|
| 5,608,526 A * | 3/1997 | Piwonka-Corle et al. | ..... | 356/369 |
| 5,841,543 A * | 11/1998 | Guldi et al. | ..... | 356/394 |
| 5,929,993 A | 7/1999 | Johs | ..... | 359/364 |
| 5,963,327 A | 10/1999 | He et al. | ..... | 359/369 |
| 7,280,209 B2 * | 10/2007 | Strocchia-Rivera | ..... | 356/369 |

* cited by examiner

*Primary Examiner* — Roy M Punnoose
(74) *Attorney, Agent, or Firm* — James D. Welch

(57) ABSTRACT

A spectroscopic system for adjusting spacing between an adjacent source/detector as a unit, and a sample, and a reflecting means for directing an incident beam which reflects from said sample back onto said sample and then into the detector along a locus which is in a plane of incidence that is offset from that of the incident beam, or directly from the reflecting means into the detector, including means for reducing reflections of a beam of electromagnetic from the back of a sample, including methodology of use.

13 Claims, 5 Drawing Sheets

US 8,159,672 B1

SAMPLE INVESTIGATING SYSTEM AND METHOD OF USE

This Application is a CIP of Ser. No. 11/452,483 Filed Jun. 14, 2006 now U.S. Pat. No. 7,623,237 and Claims Benefit from Provisional Application Ser. No. 60/691,297 Filed Jun. 17, 2005; and from Provisional Application Ser. No. 60/790,588 Filed Apr. 10, 2006.

TECHNICAL FIELD

The present invention relates to systems for investigating samples, and more specifically to a spectroscopic system which comprises means for adjusting spacing between a commonly mounted adjacent source/detector and a sample, and a reflecting means for directing an incident beam which reflects from said sample back onto said sample and then into said detector or directly into the detector, along a locus which is in a plane of incidence that is offset from that of the incident beam. The present invention further relates to reduction of reflections of a beam of electromagnetic from the back of a sample upon which it is incident at an oblique or normal angle, and especially to system and methodology for reducing such back reflections from continuously moving samples.

BACKGROUND

It is known to investigate samples with spectroscopic electromagnetic radiation. It is also known to place a source and a detector of electromagnetic radiation adjacent to one another and use reflecting means to direct an electromagnetic beam. For instance, a Patent to He et al., U.S. Pat. No. 5,963,327 describes use of a total internally reflecting prism to direct an incident beam of electromagnetic radiation progressing in a horizontally oriented plane into a vertically oriented plane so that it interacts with a sample at an intended angle of incidence, and then, via a second total internally reflecting prism redirect the reflected beam into the original horizontally oriented plane and into the detector. Said 327 Patent system enables a more compact arrangement than more conventional geometry systems which position source and detector on laterally opposite sides of a sample. It is also noted that the 327 Patent system positions an aperture at the input to the detector.

Said 327 Patent system separates the incident and reflected beams by positioning the total internally reflecting prisms which intercept the incident and reflected beams, (with respect to the sample), at some distance apart from one another. And, it is noted that two such reflective means are necessary.

Also noted is a Patent to Johs, No. 5,929,993, which describes a total film retardance monitoring system and method of use, in which a monitored film is transferred between feed and take-up reels.

It would be of benefit if a single reflecting means could be utliized in a system which positions source and detector adjacent to one another, and if there was no necessity of changing the locus of the beam into an orthogonally related plane.

It is also known that when a beam of electromagnetic radiation is caused to impinge on the surface of a sample at an oblique or normal angle, reflected electromagnetic radiation from said sample generally contains components not only from its surface, but also from the backside thereof. The effect of said backside reflections can be difficult to model, and makes characterization of surface films far more difficult, even essentially impossible. It is therefore desirable to reduce of eliminate the presence of said backside reflections.

DISCLOSURE OF THE INVENTION

The presently disclosed invention comprises a system for monitoring samples comprising:
  a source of spectroscopic electromagnetic radiation;
  a means for supporting a sample;
  a reflecting means; and
  a detector of spectroscopic electromagnetic radiation.
Said source and detector are mounted to a common support and laterally offset from one another such that in use an incident beam of electromagnetic radiation, from said source thereof, is caused to approach a sample placed on said means for supporting a sample at an intended angle of incidence along a first locus, reflect from said sample interact with said reflecting means and proceed along a selection from the group consisting of:
  again interact with said sample and re-reflect therefrom at the intended angle of incidence, then proceed along a second locus and enter said detector; and
  proceed along a second locus and enter said detector.
Said beam is also caused to pass through an intensity controlling means either before or after interaction with a sample.

Where the beam which reflects from said sample interacts with said reflecting means and again interacts with said sample, re-reflects therefrom at the intended angle of incidence, and then proceeds along a second locus and enter said detector, it is noted that said sample is tipped in plane of incidence so as to direct said electromagnetic beam which re-reflects from said sample at said intended angle of incidence, along said second locus which is offset from said the locus of said incident beam.

Said presently disclosed invention further comprises means for controlling the distance between said source and detector which are mounted to a common support, and said means for supporting a sample. Said means for controlling the distance between said source and detector which are mounted to a common support, and said means for supporting a sample cna be means for controlling either or both the position of said common support and the position of said means for supporting a sample.

A preferred arrangement provides that both said source of spectroscopic electromagnetic radiation and detector of spectroscopic electromagnetic radiation are mounted in a common enclosure, and that said common enclosure comprises means for purging volume therewithin with externally entered air or gas.

The intensity controlling filter means can be selected from the group consisting of:
  electronic gain control means in the detector;
  a neutral density filter; and
  a low pass filter.
Further, said intensity controlling filter means can comprises a selection from the group consisting of:
  at least one element which can be inserted into and removed from the locus of said incident beam of electromagnetic radiation; and
  a rotatable element which is inserted into the pathway of the locus of said incident beam of electromagnetic radiation, said rotatable element presenting said incident electomagnetic beam with different degrees of intensity attenuation at different rotation amounts.
Said presently disclosed invention can also comprise means for providing a purging flow of gas during data acquisition to least at one selection from the group consisting of:

said sample; and
said reflecting means;

A method of investigating a sample comprising the steps of:

a) providing a system for monitoring samples as described above;

b) causing said distance between said common support and said means for supporting a sample to be increased and positioning a standard sample on said means for supporting a sample, then causing said distance between said common support and said means for supporting a sample to be decreased;

c) causing an incident beam of electromagnetic radiation from said source thereof to pass through said intensity controlling means, approach a sample placed on said means for supporting a sample at an intended angle of incidence along a first locus, reflect from said sample, interact with said reflecting means, then, after optionally again interacting with said sample, proceed along a second locus and enter said detector;

d) adjusting said intensity controlling filter means such that said detector provides a non-saturated signal;

e) causing said common support and said means for supporting a sample to be increased and positioning a test sample on said means for supporting a sample, then causing said distance between said common support and said means for supporting a sample to be decreased;

f) adjusting said intensity controlling fliter means such that said detector provides a non-saturated signal; and g) analyzing data provided by detector.

The present invention further provides an approach to investigation of samples which reduces the effect of back reflections. A system for accomplishing this provides:

a sample;
a means for supporting a sample;
a source of a beam of electromagnetic radiation; and
a detector of said beam of electromagnetic radiation;
wherein said means for supporting a sample is present directly under said sample at the location thereof whereat, during use, a beam of electromagnetic radiation provided by said source thereof is caused to impinge thereupon at an oblique or normal angle of incidence. Said means for supporting a sample and said sample can be characterized by a selection from the group consisting of:

having essentially matched indices of refraction; and
having liquid present at the interface therebetween which is essentially index essentially matched to that of said sample.

Said sample and said means for supporting a sample can be variously rigid or flexible, and an important application of the present invention system is where relative motion therebetween is continuous. This can occur, for instance, where the sample is a ribbon or sheet which is continuously pulled over the means for supporting a sample. In such a case, said means for supporting a sample can be a roller characterized by a selection from the group consisting of:

it is rigid; and
it is deformable.

For instance, where a sample is rigid, benefit derives from using a deformable means for supporting a sample in order to facilitate effecting a good contact therebetween. This point is less important, though not irrelevant however, where the sample is flexible and can conform to the shape of said means for supporting a sample, and/or in the case where liquid is caused to be present between said sample and said means for supporting a sample.

It is noted that index matching need not be perfect to achieve beneficial results.

It is also noted that the methodology can involve performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

And finally, it is noted that the methodology can be carried out under the control of a computer, including control of ellipsometer or the like operation.

The present invention will be better understood by reference to the Detailed description Section of this Application, in combination with the Drawings.

DETAILED DESCRIPTION

Figure 1:
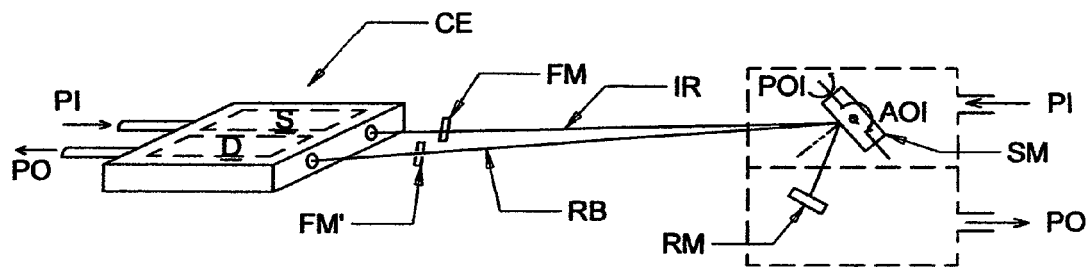
FIG. 1 shows a preferred embodiment of the system of the presently disclosed invention.

Turning now to FIG. 1, there is shown a Source (S) and Detector (D) in a Common Enclosure (CE), a Sample (SM) and a Reflective Means (RM). Note that an Incident Beam (IB) is shown impinging on said Sample (SM) along one locus, reflecting therefrom, interacting with the Reflecting Means (RM), again reflecting from said Sample (SM) and proceeding along a second locus to said Detector (D) along a second locus. Note that the Second Locus of the Reflected Beam (RB) is effected by a set rotation of the Sample (SM) about the axis identified by (POI), such that the entry to Detector (D) for the Reflected Beam (RM) is offset, above or below, the Source (S) of said Incident Beam (IB).

Figure 2:
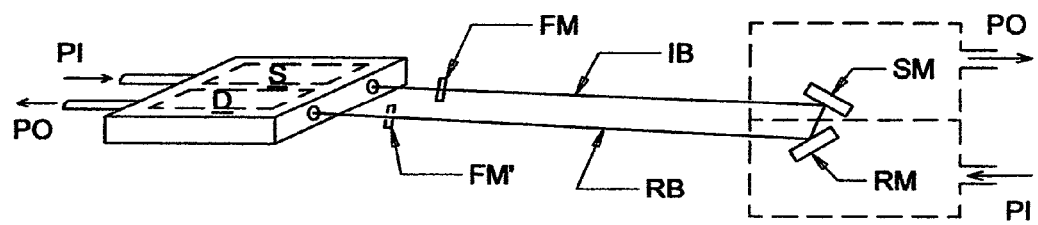
FIG. 2 shows a modified embodiment of the system of the presently disclosed invention.

FIG. 2 shows a variation of the presently disclosed invention system. Note that the Reflecting Means (RM) is oriented not to direct the Incident Beam (IB) which reflects from the Sample (SM) back onto the Sample (SM), but rather directly toward the Detector (D) as Beam (RB). In this configuration there is no requirement that the plane of incidence of the sample be rotated, as demonstrated in the FIG. 1 configuration by (POI), although it, of course, could be so rotated.

Both FIGS. 1 and 2 show the presence of an intensity controlling means (FM) which is present to condition the intensity of the electromagnetic beam. This is to avoid saturation of the Detector electronics. Note that the intensity control means (FM') could be present on the Detector (D) side.

Note in both FIGS. 1 and 2, the optional presence of Purging gas flow means (PI) and (PO). Flowing a gas can serve to cool and to provide a non-absorbing ambient for IR and UV wavelengths, for instance, in the Common Enclosure (CE). Likewise note the optional presence of means for purging the Sample (SM) and/or Reflecting Means (RM).

Figure 3A:
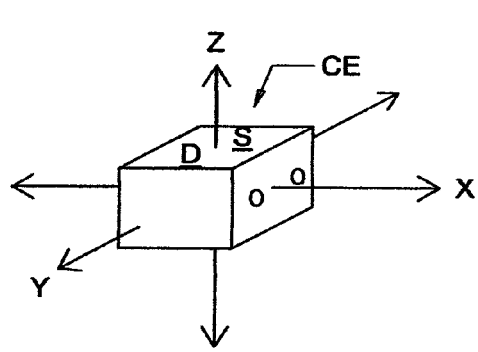
FIGS. 3a and 3b show that means for enabling relative motion of source/detector and sample/reflecting means can be employed in the system of the disclosed invention.
Figure 3B:
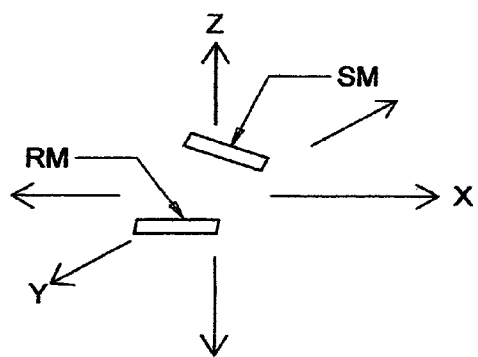
Figure 4:
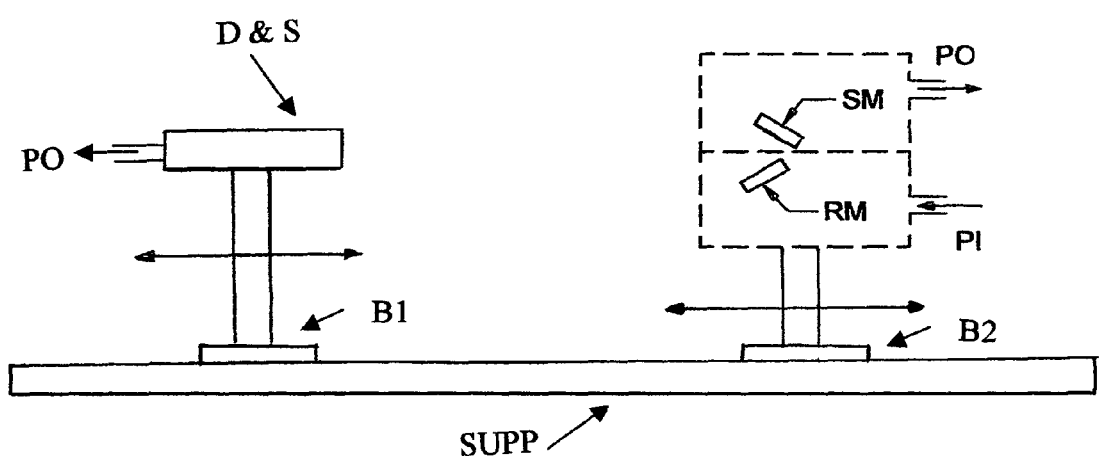
FIG. 4 shows means for controlling the distance between said source and detector, which are mounted to a common support, and said means for supporting a sample.

FIGS. 3*a* and 3*b* indicate that the adjacent Source (S) and Detector (D) as a unit and/or the Sample (SM) and Reflecting Means (RM) as a unit can be mounted to allow relative motion therebetween. This can be useful when it is necessary to mount different samples, for instance, a standard sample followed by a test sample. FIG. 4 specifically shows demonstrative means (B1) (B2) for controlling the distance between said source (S) and detector (D), which are mounted to a common support, and said means for supporting a sample (SM). Said demonstrative means (B1) (B2) are shown sitting atop a common support (SUP), and can said (B1) and/or (B2) be moved with respect thereto.

Continuing, FIGS. 5-8 demonstrate samples (SM) which can be investigated by the present invention system, including means to reduce back side reflections. As disclosed in the foregoing, the system generally comprises a Source (S) and Detector (D) as a unit, and a Sample (SM). The system in FIGS. 5-8 is further show that:
said sample (SM) has top (S1) and bottom (S2) surfaces;
there is a means for supporting (R) said sample (SM) having an outer surface (S3); and
said source (PSG) is shown as a polarization state generator of a beam of electromagnetic radiation (EMI) and said detector (PSD) is shown as being a polarization state detector and as receiving of a reflected beam of electromagnetic radiation (EMR).
Importantly, note that a portion of the beam (EMI) transmits into the sample as (EMT), and can reflect from an interface between said sample (SM) and said means for supporting (R) said Sample (SM). Said means for supporting (R) a sample (SM) is present under said sample (SM) at the location thereof whereat, during use, a beam of electromagnetic radiation (EMI) provided by said source thereof is caused to impinge thereupon at an oblique or normal angle of incidence. Also note that said means for supporting (R) a sample (SM) and said sample (SM) are characterized by a selection from the group consisting of:
having matched indices of refraction (FIGS. 5 and 6); and
having liquid (L) present at the interface therebetween which is essentially index matched to that of said sample (SM).
Said means for supporting (R) and said sample (SM) can each be rigid or deformable.

A method of monitoring reflections of electromagnetic radiation caused to impinge on the surface of a sample (SM) at an oblique or normal angle of incidence, while substantially preventing backside reflections therefrom from complicating the results, comprising the steps of:
a) providing a system comprising:
a sample (SM);
a means for supporting (R) a sample (SM);
a source (PSG) of a beam (EMI) of electromagnetic radiation; and
a detector (PSD) of said beam (EMR) of electromagnetic radiation;
wherein said means for supporting (R) a sample (SM) is present directly under said sample (SM) at the location thereof whereat, during use, a beam (EMI) of electromagnetic radiation provided by said source (PSG) thereof is caused to impinge thereupon at an oblique or normal angle of incidence;
said means for supporting (R) a sample and said sample being characterized by a selection from the group consisting of:
having matched indices of refraction; and
having liquid (L) present at the interface therebetween which is essentially index essentially matched to that of said sample (SM);
b) causing said source (PSG) of a beam of electromagnetic radiation to provide a beam (EMI) of electromagnetic radiation to impinge on a surface of said sample (SM), at an oblique or normal angle of incidence;
c) monitoring electromagnetic radiation reflected (EMR) from said sample (SM) surface which enters said detector (PSD).

Figure 5:
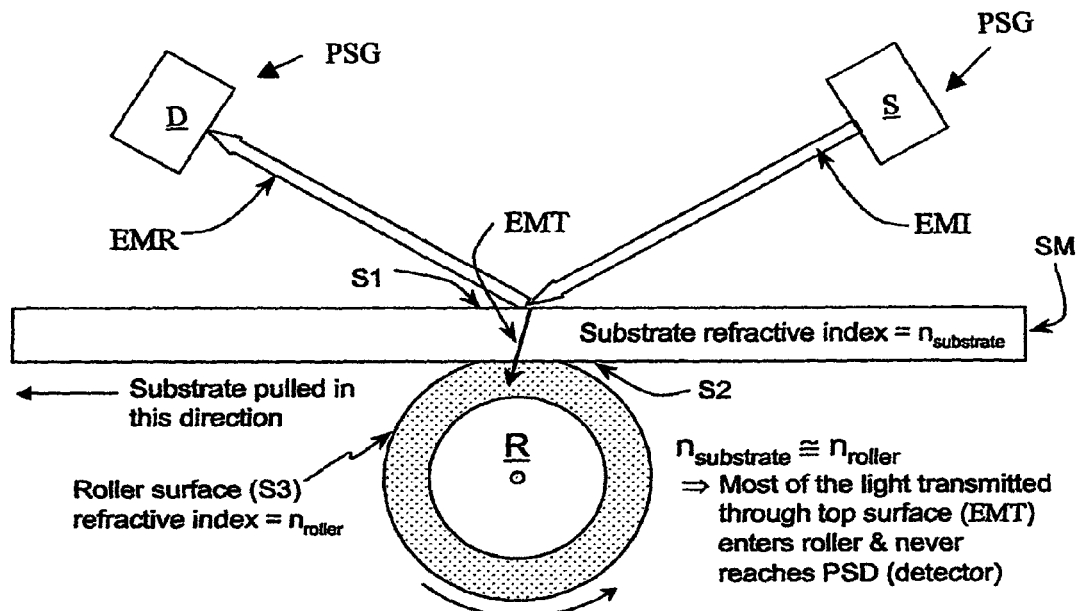
FIGS. 5-8 demonstrate samples which can be investigated by the present invention system, including means to reduce back side reflections.
Figure 6:
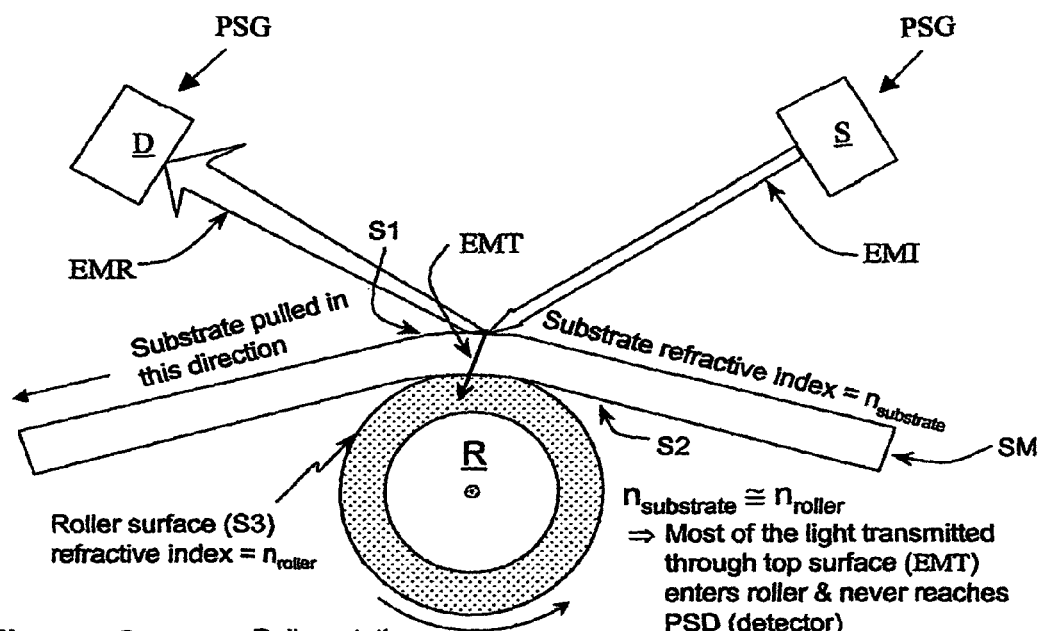
Figure 7:
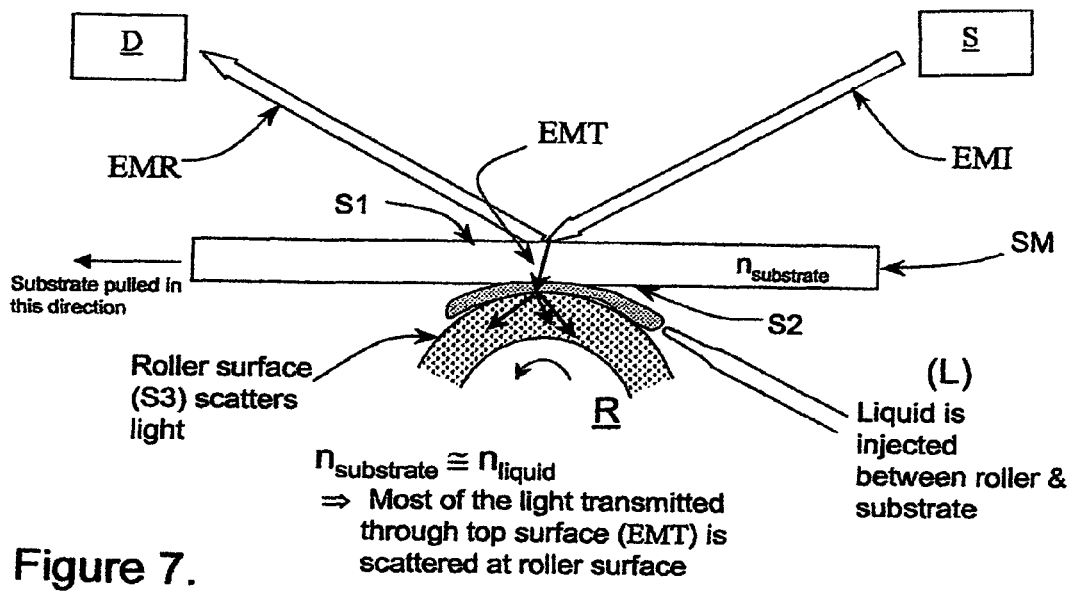
Figure 8:
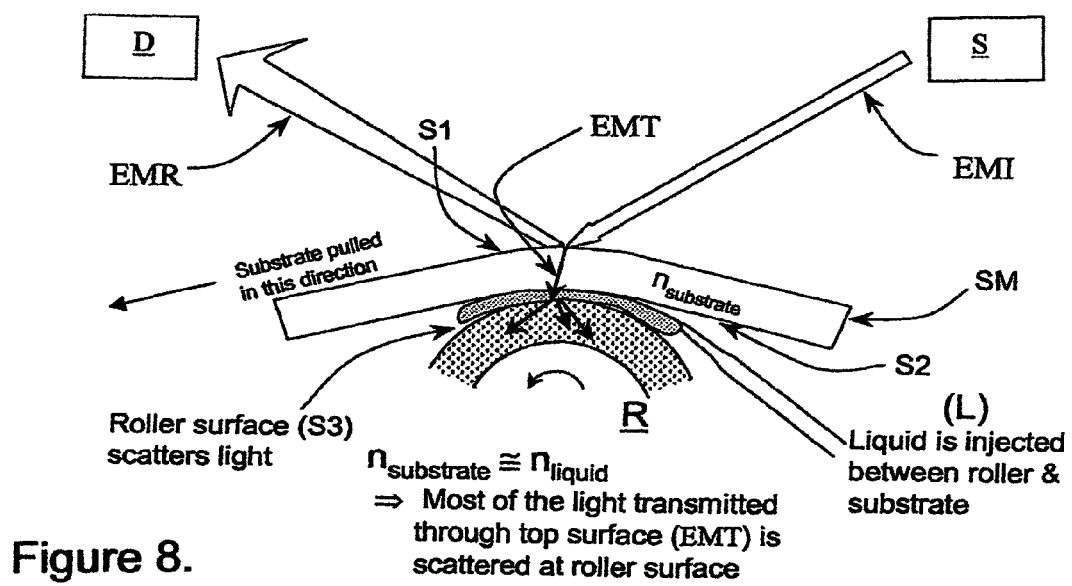

It is also to be understood that the (PSG) and (PSD) in FIGS. 5 and 6 can be rotated in position about a normal to the sample (SM) through 0-360 degrees so that the plane formed thereby is oriented as shown, or in any such rotated position.

Figure 9:
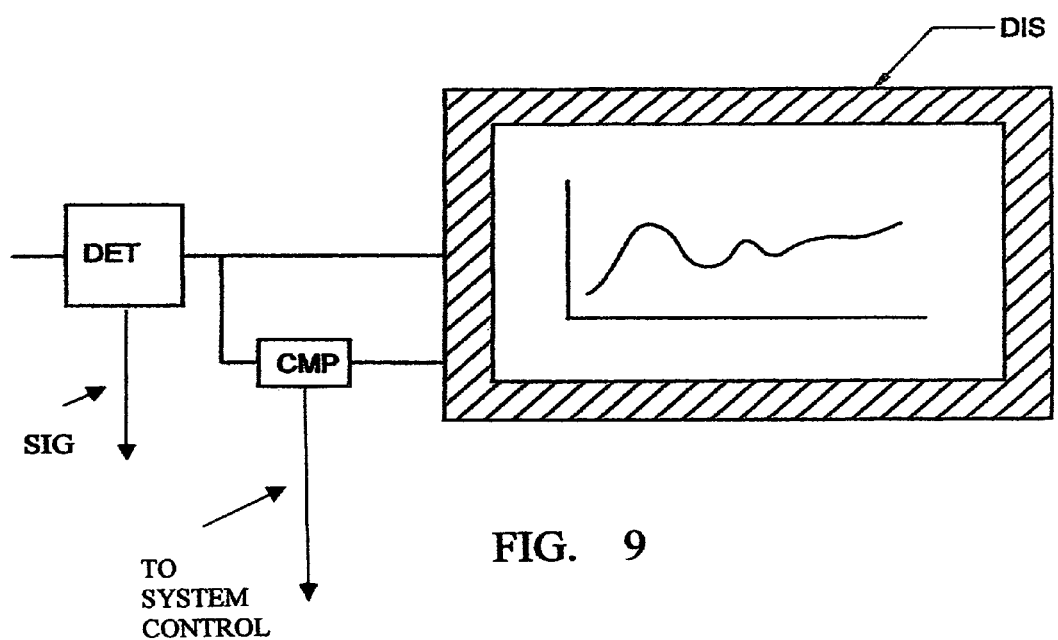
FIG. 9 demonstrates display of data, and that the methodology and ellipsometer or the like can be operated under the control of a computer.

FIG. 9 demonstrates display (DIS) of data produced by the detector (DET), and that the methodology and ellipsometer or the like can be operated-under the control of a computer (CMP).

Also, a signal (SIG) developed by the computer (CMP) can be used to cause any number of effects, as better discussed in the Disclosure of the Invention Section Section of this Specification.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of investigating a sample comprising the steps of:
a) providing a system for monitoring samples comprising:
a source of spectroscopic electromagnetic radiation;
a means for supporting a sample;
a reflecting means;
a detector of spectroscopic electromagnetic radiation; and
an intensity controlling filter means;
said source and detector being mounted to a common support and laterally offset from one another, such that in use an incident beam of electromagnetic radiation from said source thereof is caused to approach a sample placed on said means for supporting a sample at an intended angle of incidence along a first locus, reflect from said sample interact with said reflecting means and proceed along a selection from the group consisting of:
again interact with said sample and re-reflect therefrom at the intended angle of incidence, then proceed along a second locus and enter said detector; and
proceed along a second locus and enter said detector;
said beam also being caused to to pass through said intensity controlling means;
said system further comprising means for controlling the distance between said source and detector which are mounted to a common support, and said means for supporting a sample;

b) causing said distance between said common support and said means for supporting a sample to be increased and positioning a standard sample on said means for supporting a sample, then causing said distance between said common support and said means for supporting a sample to be decreased;

c) causing an incident beam of electromagnetic radiation from said source thereof to pass through said intensity controlling means, approach a sample placed on said means for supporting a sample at an intended angle of incidence along a first locus, reflect from said sample, interact with said reflecting means, then, after optionally again interacting with said sample, proceed along a second locus and enter said detector;

d) adjusting said intensity controlling fliter means such that said detector provides a non-saturated signal;

e) causing said common support and said means for supporting a sample to be increased and positioning a test sample on said means for supporting a sample, then causing said distance between said common support and said means for supporting a sample to be decreased;

f) adjusting said intensity controlling filter means such that said detector provides a non-saturated signal; and g) analyzing data provided by detector.

2. A method as in claim 1, in which said provided sample and means for supporting a sample have matched indicies of refraction.

3. A method as in claim 1, which further comprises performing at least one selection from the group consisting of:
   storing at least some data provided by said data detector in machine readable media;
   analyzing at least some of the data provided by said data detector and storing at least some of the results of said analysis in machine readable media;
   displaying at least some data provided by said data detector by electronic and/or non-electronic means;
   analyzing at least some of the data provided by said data detector and displaying at least some of the results of said analysis by electronic and/or non-electronic means;
   causing at least some data provided by said data detector to produce a signal which is applied to provide a concrete and tangible result;
   analyzing at least some of the data provided by said data detector and causing at least some thereof to produce a signal which is applied to provide a concrete and tangible result.

4. A method as in claim 1, in which control of the system for monitoring samples is under control of a computer.

5. A method of monitoring reflections of electromagnetic radiation caused to impinge on the surface of a sample at an oblique or normal angle of incidence, while substantially preventing backside reflections therefrom from complicating the results, comprising the steps of:
   a) providing a system comprising:
      a sample;
      a means for supporting a sample;
      a source of a beam of electromagnetic radiation; and
      a detector of said beam of electromagnetic radiation;
   wherein said means for supporting a sample is present directly under said sample at the location thereof whereat, during use, a beam of electromagnetic radiation provided by said source thereof is caused to impinge thereupon at an oblique or normal angle of incidence;
   said means for supporting a sample and said sample being characterized by a selection from the group consisting of:
      having matched indices of refraction; and
      having liquid present at the interface therebetween which is essentially index essentially matched to that of said sample;
   b) causing said source of a beam of electromagnetic radiation to provide a beam of electromagnetic radiation to impinge on a surface of said sample, at an oblique or normal angle of incidence;
   c) monitoring electromagnetic radiation reflected from said sample surface which enters said detector.

6. A method as in claim 5, wherein said sample is a sheet or ribbon and is caused to move over said means for supporting a sample while said reflected electromagnetic radiation from said sample surface enters said detector.

7. A method as in claim 6 wherein said step of providing a sample involves providing a sample that is flexible.

8. A method as in claim 6 wherein said step of providing a sample involves providing a sample that is rigid.

9. A method as in claim 6 wherein said step of providing a means for supporting a sample involves providing a means which is rigid.

10. A method as in claim 6 wherein said step of providing a means for supporting a sample involves providing a means which is deformable.

11. A method as in claim 6, wherein both:
    legs 3 and 5 and associated vertically oriented legs, and
    legs 4 and 6 and associated vertically oriented legs;
    form parallelograms.

12. A method as in claim 5, which further comprises performing at least one selection from the group consisting of:
    storing at least some data provided by said data detector in machine readable media;
    analyzing at least some of the data provided by said data detector and storing at least some of the results of said analysis in machine readable media;
    displaying at least some data provided by said data detector by electronic and/or non-electronic means;
    analyzing at least some of the data provided by said data detector and displaying at least some of the results of said analysis by electronic and/or non-electronic means;
    causing at least some data provided by said data detector to produce a signal which is applied to provide a concrete and tangible result;
    analyzing at least some of the data provided by said data detector and causing at least some thereof to produce a signal which is applied to provide a concrete and tangible result.

13. A method as in claim 5, in which control of the system for monitoring samples is under control of a computer.

* * * * *